United States Patent [19]

Stodolsky

[11] Patent Number: 5,032,502
[45] Date of Patent: Jul. 16, 1991

[54] PURIFICATION OF POLYMORPHIC COMPONENTS OF COMPLEX GENOMES

[75] Inventor: Marvin Stodolsky, Germantown, Md.

[73] Assignee: The United States of America as represented by the United States of Energy, Washington, D.C.

[21] Appl. No.: 146,508

[22] Filed: Jan. 21, 1988

[51] Int. Cl.$^5$ .................. C12Q 1/68; C07H 15/12; C12N 15/00
[52] U.S. Cl. .......................... 435/6; 536/27; 935/77; 935/78
[58] Field of Search ................ 435/6; 536/27; 935/77, 935/78

[56] References Cited

U.S. PATENT DOCUMENTS 4,283,489 8/1981 Goodman et al. ................ 435/6
4,861,708 8/1989 Frossard ........................ 435/6

OTHER PUBLICATIONS

Yokota et al., Proc. Natl. Acad. Sci., U.S.A., vol. 87, pp. 6398-6402, Aug. 1990.
Roninson, Nucleic Acids Research, pp. 5413-5431 (1983).

Primary Examiner—Robert A. Wax
Assistant Examiner—Mindy B. Fleisher
Attorney, Agent, or Firm—James W. Weinberger; Thomas G. Anderson; William R. Moser

[57] ABSTRACT

A method is disclosed for processing related subject and reference macromolecule populations composed of complementary strands into their respective subject and reference populations of representative fragments and effectuating purification of unique polymorphic subject fragments.

20 Claims, 1 Drawing Sheet

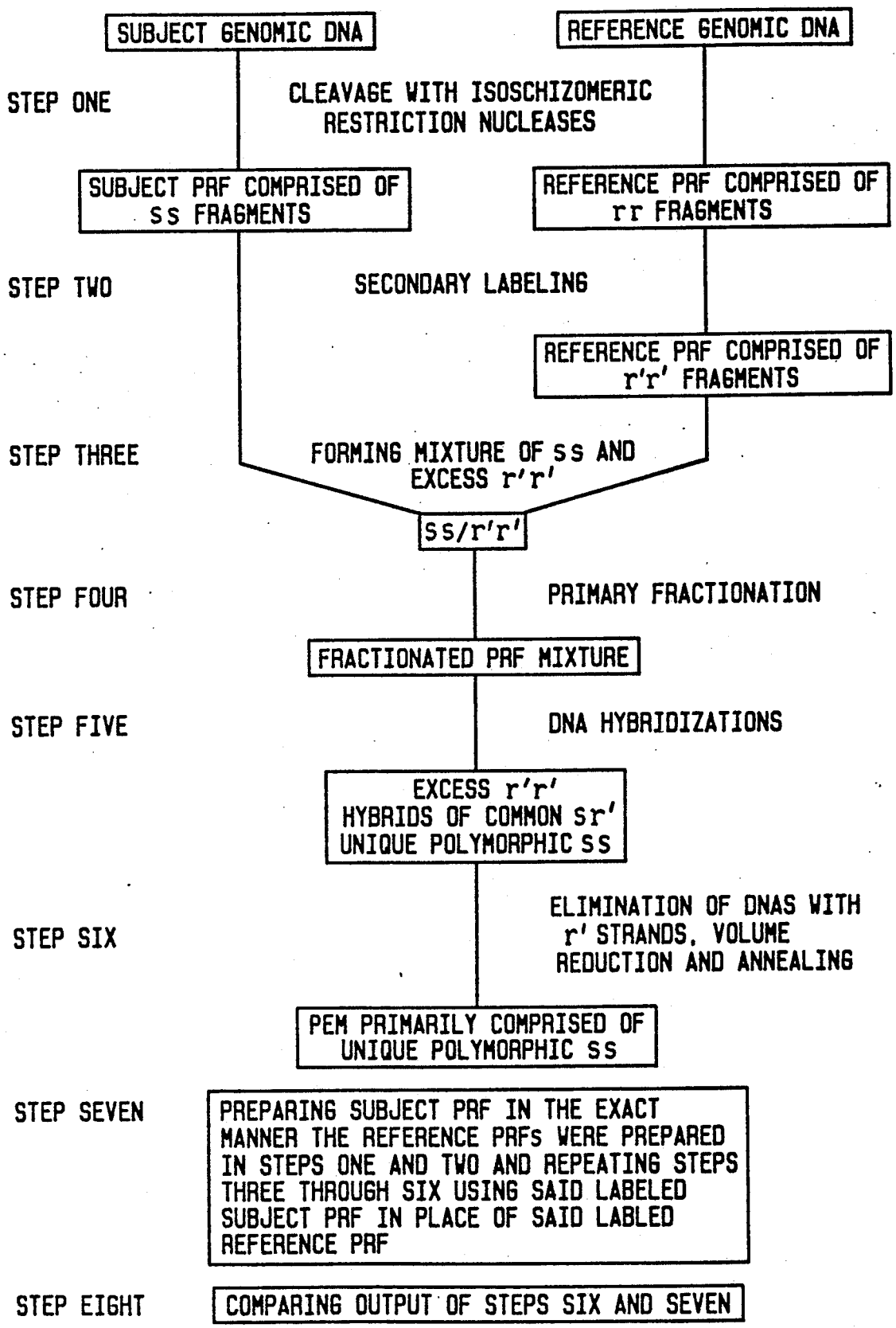

PURIFICATION OF POLYMORPHIC COMPONENTS OF COMPLEX GENOMES

CONTRACTUAL ORIGIN OF THE INVENTION

Part of the work leading to this invention was made with United States Government support. The United States Government has certain rights in this invention pursuant to contract number DE-AC02-86CH10303 between the Department of Energy and Argonne National Laboratory.

BACKGROUND OF THE INVENTION

This invention is generally related to a method of characterizing macromolecules composed of complementary strands. More specifically the invention concerns a method for subtractive comparisons of populations of representative fragments (hereinafter PRFs) representing two related complex macromolecules such as genomic DNA and RNA and partial purification of polymorphic PRF components in which the two macromolecules differ.

Polymorphisms are genetic differences between two related genomes which are inheritable and contribute to the diversity within a species. They correspond to subunit structural differences in the DNAs (or RNAs) which encode the genome. Many DNA polymorphisms are without manifest physiological effects, while others are causal factors for inherited traits, whether the effects be positive, neutral or causative for genetic disease. Therefore, the isolation of fragments of the total genomic DNA which represent polymorphism sites is an important task of biological and medical research. For medical genetics, these fragment isolations constitute one step in the development of capacities to diagnose genetic diseases. More generally, it is a common constituent of biological research programs to isolate genes and characterize their functions.

Previously, the detection of genetic differences in genomic DNA and the isolation of genes has been limited by the complexity of genomes which could be analyzed by conventional procedures without resorting to laborious comparative probing techniques. The following is a discussion of some of those procedures and their drawbacks.

Subtraction hybridization was one of the first approaches used in the isolation of genes or their corresponding RNA. This process relies on the duplex or double stranded structure of DNA and RNA/DNA hybrids. DNA duplexes can be denatured, i.e., separated into their complementary strands by treatment with heat or with destabilizing agents, such as a formamide or a high pH solution. Annealing conditions can be established under which strands pair up and reform duplexes. The stability of the duplexes is highly dependent on proper pairing of constituent bases across the strands. The four constituent bases found in DNA molecules are adenine, thymine, guanine, and cytosine (hereinafter, abbreviated A, T, G, and C, respectively). Proper subunit pairings across the strands are A with T and G with C. In the first subtraction hybridization experiments, viral subject DNA and host cell DNA were utilized. The viral component of the total RNA extracted from the virus infected cells was selectively bound to viral, but not to host cell DNA. (Bautz and Hall, *The Isolation of T4-Specific RNA on a DNA-Cellulose Column,* 48 Pro. Nat. Acad. Sci. 400 (1962)). Hybridization will occur between two complementary single strands even if one of the strands is stably attached to a matrix.

During conventional subtraction hybridization, DNAs of a subject genome and a related reference genome are utilized. The duplex DNAs of both are fragmented and then denatured. Fragmented reference strands are bound to a matrix, such as agarose, cellulose or nylon. Fragmented subject strands are annealed with a large molar excess of the bound reference strands. During the annealing process, most of the subject strands pair with reference complements and are entrapped in hybrid duplexes of subject and reference strands. Subject strands without reference complements cannot pair off in a stable duplex with, and thereby be entrapped by, the reference DNAs. After the annealing step, removal of the matrix eliminates reference DNAs and the entrapped homologous subject DNAs. The free subject DNAs are comprised of the sought unique subject DNAs and common DNAs which have escaped entrapment in hybrid duplexes. The former comprise a much greater proportion of the free DNAs than they did of the input subject DNA population, since the majority of the common DNAs have been subtracted out. The net subtraction hybridization process thus provides a partial purification for the sought unique DNAs lacking reference complements.

The extent of elimination of the unwanted subject DNAs during a conventional subtraction hybridization process depends on the molar ratio of the input materials. The annealing of strands into duplexes is a bimolecular reaction obeying conventional chemical mass action laws. With an input ratio of one subject DNA to ten reference DNAs, the annealed products are in the ratio of 0.1 (subject): 2 (hybrid): 9 (reference duplexes). Thus, with respect to the input subject DNA population, the elimination of matrix bound DNAs eliminates 90% of the subject DNA with reference homologies.

Conventional subtraction hybridization technology has limited applicability, i.e., polymorphisms corresponding to deletions in the genomes of simple organisms such as viruses and bacteria. The technique fails for point mutations and rearrangement polymorphisms. The subject DNA polymorphisms being sought still have homologies with the reference DNAs, and would consequently be entrapped and eliminated during a subtraction hybridization procedure. Moreover, genomic DNA of higher species contains numerous base pair sequences which are repeated and dispersed throughout the chromosomes. For example, about 80% of human genomic DNA is comprised of several families of repeated (reiterated) DNA sequences, the largest families having hundreds to thousands of copies. Single copy genes or sequences comprise the remaining 20% of human genomic DNA. The reiterated sequences cause an undesirable complication. During an annealing of DNA strands of a complex genome, the reiterated sequences make more rapid contacts than the much lower concentration single copy sequences. Consequently, reiterated regions form stable duplex regions, regardless of non-homology between adjacent single copy gene regions. As a result, extended "promiscuous" tangles of DNA form that are stabilized by the duplex regions. The formation of promiscuous tangles hinders the purification in conventional subtraction hybridization.

Alternative approaches to conventional subtraction hybridization utilize restriction nucleases. A restriction nuclease is an enzyme that has the capacity to recognize a specific target sequence, several base pairs in length in double-stranded DNA molecules, and to cleave both strands of the DNA molecule at the locations of target sequence. The DNA molecules defined by digestion with a restriction nuclease are referred to as restriction fragments. Any given genomic DNA digested by a particular restriction nuclease is converted into a discreet PRF.

A restriction fragment length polymorphism (hereinafter, RFLP) is a particular type of polymorphism manifested as a difference in the lengths of some genetically related fragments of the two PRFs compared. The underlying genetic manifestations can be as subtle as a single base pair change, which creates or eliminates a cleavage site, or as gross as a genetic deletion which changes the length of DNA between cleavage sites. To detect a RFLP, an analytical method for fractioning double-stranded DNA molecules on the basis of size is required. The most commonly used technique for achieving such a fractionation is agarose gel electrophoresis. In that method DNA molecules migrate through the gel which acts as a sieve that retards the movement of the largest molecules to the greatest extent and affects the movement of the smallest molecules to the least extent. A comparison of gel electrophoretically fractionated PRFs reveals the fragments unique to each genome among those common to the subject and reference PRFs compared. The unique fragments represent the RFLP. Fractionated PRFs can also be denatured and annealed within the confines of the fractionation gel. Such in situ annealings have been employed previously, in a strategy to selectively detect reiterated PRF members. (Roninson, *Detection and mapping of homologous, repeated and amplified DNA sequences by DNA renaturation in agarose gels*, 11 Nucleic Acids Res. 5413-31 (1983)).

Fractionations which distinguish compared DNAs by the stability of the base pairing have also been used (Fischer and Lerman, *Length-Independent Separation of DNA Restriction Fragments in Two-Dimensional Gel Electophoresis*, 16 Cell 191-200 (Jan. 1979)). They can reveal some polymorphisms between DNAs of the same length.

So long as a fractionation procedure can resolve the constituents of each PRF, differences between PRFs are easily detectable. For example, desired resolution can be achieved with one dimensional fractionations for many viral PRFs, or with two dimensional fractionations responsive to fragment length and thermal stability, for bacterial PRFs. However, for higher organisms, even if the best fractionation techniques are used, resolution of the sought polymorphic PRF constituents is not achieved. With such higher organisms, separation of any single member from the majority of the PRF membership occurs, but there are so many members that there is a continuum of overlapping fragment bands which prevents resolution and detection of members within the continuum.

When there is a continuum of fragment bands, probing techniques have been used to display positions of particular genes. A cloned form of the gene which is sought is given a radioactive or biochemical label that can be later employed to reveal its position. It serves as a probe to locate its homologues. The fractionated subject DNAs are denatured into constituent strands and then transferred and stably bound to a membrane, e.g., blotted onto a stable membrane. Single stranded probe and blotted subject DNAs are then annealed. The probe binds in a stable manner by base pairing, only at the position of its genetic homologues, and the positions of homologous fragments on the blot, are thereby detected. With most single gene probes, the compared PRFs show no differences for the fragments selectively displayed. Nevertheless, laborious comparative probings of related PRFs can be sequentially performed and with a large enough population of probes, polymorphisms useful for genetic diagnostic purposes can eventually be detected. (Gusella et al., *A Polymorphic DNA Marker Genetically Linked to Huntington's Disease*, 306 Nature 234 (1983)).

Another technique has been used to selectively display a sub-population of polymorphisms of viral genomic DNA. In this technique, the PRFs of the genomic DNA of two genomes to be compared are prepared. They are pooled in equal amounts and hybridized. Hybridization products are then treated with nuclease S1 which cleaves at distortions in DNA duplexes. (Shenk et al., *Biochemical Method for Mapping Mutational Alterations in DNA with S1 Nuclease: The Location of Deletions and Temperature-Sensitive Mutations in Simian Virus 40*, 72 Proc. Nat. Acad. Sci. 3:989-993 (1975)). Some hybrid duplexes comprised of polymorphic DNA strands have a sufficient degree of distortion and are consequently cleaved at these sites. Secondary fragments thus generated are detected through a fractionation, during which S1 cleavage fragments migrate faster than intact predecessor fragments. It is essential for this distortion cleavage technique that a control consisting of a hybridization of each PRF against itself is conducted for comparative analysis of the products. Such controls do yield secondary S1 fragments which arise because of partial homologies and reiterated sequences within the genomic DNA. The fragments encoding them form distorted duplexes and partially duplex complexes during hybridizations. Thus, secondary fragments arise during the S1 nuclease digestion. These secondary fragments must be identified in order to distinguish polymorphisms between genomes from internal homologies within a genome. This distortion cleavage technology has also been used with bacterial genomic DNA. (Yee and Inouye, *Two-dimensional S1 nuclease heteroduplex mapping: Detection of rearrangments in bacterial genomes*, 81 Proc. Nat. Acad. Sci. 2723-2727 (1984)). Internal homologies are a small fraction of the total genomic DNA in bacterial genomes and are identifiable from the control. By contrast, internal homologies are extensive in the genomic DNA of higher organisms. As a consequence when this technique is used with PRFs of higher organisms, the sought polymorphisms are obscured by the great abundance of secondary fragments arising as a consequence of the extensive internal homologies.

Other polymorphism identification techniques have been used with a very limited domain of utility. These are techniques which require the prior cloning of the genome fragment whose polymorphisms will subsequently be sought. The most refined of these methodologies is comparative nucleotide sequencing, through which the particular subunit differences of the polymorphism are identified.

BRIEF SUMMARY OF THE INVENTION

It is therefore an object of the invention to provide a new method for detection of at least one difference between two related macromolecules composed of complementary strands (hereinafter macromolecules) such as, for example, duplex DNA and duplex RNA.

Another object of the invention is to provide a novel method for obtaining simultaneous partial purification of many unique members of the PRF of the subject macromolecules which lack complements in the fragments of the reference macromolecules.

A third objective of the invention is to provide a new method of identifying extrinsic additions to and rearrangements within a subject genomic DNA, as compared with an appropriate reference genomic DNA.

A feature of the invention is a method which enables partial purification and subsequent detection of a class of unique members of the PRF of the subject genomic DNA from members common to the subject and reference PRFs, even when the PRFs are so complex that fractionation does not itself resolve constituent members within each PRF. A single PRF member is the set of genetically identical fragments, corresponding to identical segments of the multiple identical substrate genomes, generated by the site specific cleavages of the substrate genomes. The class of unique members of the compared PRFs is determined by the particular fractionation procedure chosen. Such fractionation procedures would include, for example, separation by fragment length, average subunit composition, initiation of double helix to single strand transition, termination of the double helix to a single strand transition and capacity to bind any of a variety of agents. The chosen primary fractionation achieves a separation of any particular PRF member from most of its companion input into the fractionation. PRF members from corresponding genetic loci of subject and reference genomic DNA which do not cofractionate will be in the pool of polymorphic members purified through the method of the invention. For example, if members derived from corresponding loci for subject and reference genomic DNA differ in length (i.e., are RFLP), the method of the invention will yield subject members representing the RFLP loci.

The invention is also able to overcome the problems presented by an abundance of repeated sequences, which is a characteristic of higher eukaryotic organisms (organisms whose cells contain nuclei). This is accomplished by performing the above fractionation prior to a subtractive hybridization. The fractionation distributes the PRF members including those with repeated sequences into numerous distinct fractions. With the complexity of each fraction being much less than that of the total input PRFs, the potential for promiscuous complex formation within each fraction is accordingly much reduced during the subsequent substractive hybridization. The invention is able to overcome problems of random DNA breakage during the above processing through the inclusion of steps dependent upon the presence of the original pairs of fragment ends generated during the reduction of genomic DNAs to their PRFs.

In the preferred form of the invention, the process is generally directed to (1) converting the subject and reference genomes into their respective PRFs; (2) providing the subject and reference PRFs with distinct biochemical and/or isotopic labels; (3) forming a mixture of the subject PRF and reference PRF; (4) fractionating the mixture; (5) denaturing the fragments within each fraction into single DNA strands and annealing the strands to reform duplexes, which include (a) hybrid duplexes of strands common to both the subject and reference PRFs, (b) residual subject fragments which are unique to the subject PRF, and (c) excess reference fragments; (6) utilizing the distinct biochemical and/or isotopic labels for purifying the subject fragments which have not been captured in duplexes with their reference homologues, thereby providing the desired partial purification of the fragments unique to the subject PRF; (7) performing a control purification on subject PRF alone; and (8) comparing the product of step 7 with the product of step 6 to identify non-polymorphic subject fragments still present in the partially purified product of steps 1-6. Other standard methodologies can then be employed to further characterize and obtain complete purification of the PRF members representing polymorphisms.

The invention, together with further objects and attendant advantages thereof, will be best understood by reference to the following description taken in connection with the accompanying drawing.

BRIEF DESCRIPTION OF THE DRAWING

The novel features of the invention are set forth in the appended claims. The invention itself, however, together with further objects and attendant advantages thereof, will be best understood by reference to the following description taken in connection with the accompanying drawing in which: FIG. 1 is a process flow diagram illustrating a method for partially purifying unique PRF constituents.

DETAILED DESCRIPTION OF PREFERRED EMBODIMENTS

Referring now to the drawing, a process flow diagram illustrates one form of the invention for the subtractive comparison of two PRFs representing the genomic DNA of two related genomes and for the partial purification of restriction fragments of the subject genomic DNA which are not represented in the PRF of the reference genomic DNA. In the initial step of the process, one of two related genomes is designated the subject genome and the other is designated the reference genome. The genomic DNA of the two genomes are converted into their respective subject and reference populations of representative fragments (hereinafter, subject and reference PRFs). The conversion of each genomic DNA into a PRF is accomplished by cleaving the duplex DNA molecules with any conventional restriction nuclease or by any other method of cleavage which yields defined fragments, as opposed to randomly broken strands.

In the preferred embodiment the subject and reference genomic DNA are converted in the initial step into their respective PRFs using conventional isoschizomeric nucleases. Restriction nucleases which recognize the same target sequence in a double-stranded DNA molecule, but cleave the strands at different base residues are isoschizomers of each other. For example, the conventional restriction nuclease Asp718 recognizes the six-base pair target sequence in duplex DNA molecules:

where the dashed line represents non-target portions of the DNA strands. The Asp718 cuts the strands of the DNA molecule between the two G's. Asp718's isoschizomer, KpnI, recognizes the same base sequences but cuts identical strands of the DNA molecule between the two C's. Cleaving one of two identical samples of genomic DNA with Asp718 and the other with KpnI produces PRFs which have identical membership but different fragment ends. The Asp718 produced PRFs have

fragment ends, while the KpnI generated PRFs have

fragment ends.

In the preferred embodiment for DNA, the subject PRF is prepared with Asp718, and the reference PRF is prepared with KpnI (or vice versa). The advantage of using isoschizomers is that they label the PRFs by providing fragment end differences which enable identification of one type of fragment in the presence of others. Further the use of isoschizomers also enables selective Recombinant DNA cloning at the end of the process. The particular pair of isoschizomers, Asp718 and KpnI, is chosen for two reasons. First, the characteristic fragment ends are readily used as discriminating end labels in later steps of the method of the invention. Secondly, the six base pair target size yields PRF membership with useful size distribution for primary length fractionations. It is useful to designate duplex subject fragments as "ss" and duplex reference fragments as "rr".

The second step of the process shown in FIG. 1 is preparing the reference PRF of step one with further biochemical and/or isotopiclabels. Reference fragments with the additional labels are designated r'r'. The choice of these labels is constrained by the requirement that genetically identical ss, rr and r'r' fragments must have identical mobilities during the subsequent primary fractionation step, step number 4. The labels added in the second step enable separation of reference DNAs and DNA hybrids of subject and reference DNA strands from subject DNAs during the secondary fractionation in step six.

In the preferred embodiment, the second step involves the photodynamic biotinylation of the reference restriction fragments, i.e., using a light process to add a biotin label to the reference fragments. This step results in a second type of labeling of the reference PRF. Biotinylated DNAs can be strongly bound to a chromatography resin with attached avidin or strepavidin. Such chromatography steps enable retention of biotinylated reference DNA molecules and duplex hybrids of subject and biotinylated reference DNA strands, while non-biotinylated subject DNAs pass freely during a secondary fractionation process in step six.

In the third step of the process illustrated in FIG. 1, a mixture of the r'r' reference PRF and the ss subject PRF is formed and designated as "ss/r'r'". In this preferred embodiment, this mixture should be in quantities compatible with fractionation technique used in step four and any later amplification of polymorphic subject DNA fragments by cloning after the seventh step of the process. A high reference PRF to subject PRF ratio enhances later entrapment of subject restriction fragments components with isogenic reference restriction fragment components in duplex DNA hybrids comprised of subject and reference DNA strands. The term isogenic means encoding the same sequence of genetic material. Isogenic fragments can differ by point mutations (e.g., one base pair) but do not have substantial differences in gene content or order. This step can be carried out using a 1:1 ratio of biotinylated reference PRF to subject PRF. However, as stated above efficacy improves as the ratio increases. For example, this portion of the protocol has been carried out using a 10:1 ratio of biotinylated reference PRF to subject PRF. In the preferred embodiment even greater efficacy would be expected at ratios of 100:1 to 1000:1.

In the fourth step of the process the mixture produced in the third step is fractionated using any conventional fractionation procedure that (1) separates each particular member of a PRF from the great majority of the other constituents of that PRF and (2) allows co-migration of members genetically identical in the subject and reference PRFs, regardless of their different labels. Although it is important that each input member is partitioned from most of its companion input during the fractionation process, it is not necessary that physically overlapping zones of PRF members be resolved during fractionation. This fractionation defines two classes of subject members. The common subject members are those having co-migrating and isogenic reference partners. The unique subject members are those subject polymorphic. DNA fragments which lack isogenic and co-migrating reference partners. It is these unique polymorphic fragments which will be purified through the net, i.e., total, process.

The substantive separation of each member from most of its companion input achieves a second important objective. The separations diminish the probability that any member has co-resident members with accidental homologues including, for example, reiterated sequences. Consequently the formation of promiscuous tangles in the subsequent DNA hybridization is greatly reduced. Each member co-resides with many fewer members than in the initial PRF input.

The preferred technique for achieving fractionation of the mixture is size fractionation by electrophoresis through an agarose gel. In this technique, DNA molecules migrate through the gel as though it were a sieve that retards the movement of the largest molecules to the greatest extent and the movement of the smallest molecules to the least extent. Therefore, the smaller the restriction fragment, the greater the mobility under electrophoresis in the agarose gel. Members representing length polymorphisms in the subject PRF do not co-fractionate with partial homologues of the reference PRF, while isogenic subject and reference members do co-fractionate. The fractionation process can terminate either with the DNAs still entrapped within the gel or by collecting fractions of effluent from the process. Maintaining the DNAs within the gel best preserves the member separations achieved through the fractionation process. The term fraction is applied to zones of gel with their entrapped membership, as well as the collected fractions of effluent exiting the fractionation apparatus.

The fifth step in the process shown in FIG. 1 involves performing a DNA hybridization within each fraction formed during step four. During the DNA hybridization the fractionated restriction fragments are first denatured, i.e., the duplex restriction fragments are separated into their complementary single DNA strands using denaturing conditions, such as, for example, high pH, heat or formamide solutions. The single DNA strands are then annealed into duplexes. During this part of the DNA hybridization, common subject strands are driven into sr' hybrid duplexes with the co-resident excess complementary reference strands. In contrast, the unique members cannot be entrapped in hybrids as they lack co-resident isogenic reference DNAs. Instead these unique polymorphic strands anneal with their subject complements. Excess reference strands form duplexes with their complements. The annealing reaction rate will diminish as constituents are utilized and the concentration of reactants diminishes. As a result, the products of the annealing step include hybrid DNA duplexes, pure subject DNA duplexes, pure reference DNA duplexes, and residual single subject and reference DNA strands. Partial or complete poolings of the post-hybridization fractions may be performed in preparation for step six of the process as pooling of the DNA into size classes may facilitate later Recombinant DNA formation(s).

In the preferred embodiment the DNA hybridization is preferably done in situ, i.e., in the agarose gel used during fractionation. In situ hybridization maximally conserves the fractionations achieved in step 4 of the process and favors the formation of DNA duplexes from strands by avoiding dilutions associated with fraction collection, while preventing convective mixing with neighboring fractions.

Following DNA hybridization, the distinguishing biochemical and/or isotopic labels added to reference PRFs during step two are utilized in step six, which is the secondary fractionation step. Those labels enable a separation of the reference DNAs and DNA hybrids of subject and reference DNA strands from the subject DNAs. This step eliminates the excess of input reference DNA along with the hybrids. The result of this secondary fractionation is a partial purification of unique polymorphic members of said subject PRF. In the preferred embodiment the biotinylated reference DNAs, together with their hybrids with isogenic subject strands, are removed by chromatography over a resin with attached avidin or strepavidin, relying on the tight binding of the biotin labeled reference DNA to a matrix with bound avidin. The proportion of sought polymorphic subject PRF members among the free subject DNA is substantially increased by the removal of the common PRF components. This population of free subject DNAs is designated polymorphism enriched members (herein after, PEM).

With the above elimination of the unwanted reference and hybrid DNAs, a substantial reduction in the volume of the remaining PEM can be accomplished. This reduction in volume is highly desirable because expensive enzymalogical reagents will subsequently be needed in concentration dependent reactions for further purification steps and Recombinant DNA procedures. With the corresponding increase in subject DNA concentration, a further annealing of remaining single subject strands into duplexes can be performed.

It is expected that a portion of the common subject PRF members, along with DNA processing debris including intact and broken single strands, broken duplexes, and possibly some promiscuous tangles, will survive step 6 of the process. Together these contaminants will constitute a reduced background of common fragments within which the sought unique members must be recognized. Identification of this reduced background is provided for in steps seven and 8 of the process. Step 7 of the process involves preparing a portion of the subject PRF in the exact manner the reference PRF was prepared in steps 1 and 2 of the process. Subject fragments prepared in this manner are designated "s's'". Then a ss/s's' mixture corresponding to the ss/r'r' mixture formed in step 3 and utilized in steps 4 through 6 is formed. The s's' component of the mixture has the same termini as the r'r' of the ss/r'r' mixture in step 3 of the process. This ss/s's' mixture is then processed through the same steps 4 through 6 as the ss/r'r' mixture was. Since the ss/s's' mixture has no unique components, the output of this repetition of steps 4 through 6 is identical to the common background contaminating the PEM. This output is designated control fragment membership (hereinafter, CFM). In step 8 of the process the PEM and CFM are compared. The difference between the PEM and CFM are the sought unique polymorphic members of the subject PRF.

The object of further processing is to recognize and/or purify the unique polymorphic members of the PEM from the common background represented by the CFM. The end labels generated in step one of the process are utilized for further characterization and processing of the subject polymorphic PRF components. These characterization and processing steps can include comparative PEM and CFM display, formation of Recombinant DNAs, amplification of Recombinant DNAs, and recycling through the steps 1-7 with PEM or amplified PEM serving as the input.

During Recombinant DNA formation and amplification, a vector DNA for Recombinant DNA formation having termini that are complementary to the Asp718 produced fragment ends of the ss fragments can be utilized. Such vector DNAs cannot base pair with the hybridization contaminants nor the DNA processing debris but do base pair with and are attached by enzymatic reactions to the ss fragments to form linear molecules used as precursors for viable Recombinant DNAs. Consequently the use of the isoschizomeric fragment end differences produced in step one permits selection for and purification of the sought polymorphic ss fragments.

In another form of the invention, the method can be used to similarly process double stranded messenger RNA and other macromolecules composed of complementary strands.

The invention has the advantage of identifying and partially purifying many polymorphic members of a PRF at one time even when the PRF is so complex that conventional fractionation does not itself resolve constituent members within each PRF. It can consequently serve for the detection of genome changes which contribute to viral diseases, cancer and genetically inherited diseases. It can also serve in identification of genome changes with characteristics advantageous to agricultural and biotechnological endeavors.

The novel features characteristic of the invention are set forth in the appended claims. It should be understood that various changes and modifications to the preferred embodiments described herein will be apparent to those skilled in the art. Such changes and modifications can be made without departing from the scope and equivalents of the present invention and without diminishing its attendant advantages. It is therefore, intended that the invention and such changes and modifications be covered by the following claims.

What is claimed is:

1. In a population of double stranded nucleic acid (DNA) derived from a genome which is so complex that its members cannot be resolved by a fractionation process, a method for comparing subject and reference DNAs and effectuating partial purification of unique polymorphic subject fragments from subject and reference populations of representative fragments (PRFs), comprising the steps of:
   (a) cleaving DNAs at specific nucleotide sequences to provide respective subject and reference PRFs;
   (b) distinctively labelling each of said reference PRF;
   (c) forming a mixture of said labeled reference PRF and said subject PRF;
   (d) fractionating members of said PRFs in said mixture;
   (e) performing a hybridization of said fractionated mixture;
   (f) utilizing said distinct labels for separating said reference duplexes and hybrids of said subject and reference fragments from said subject fragments and achieving said partial purification of said polymorphic subject fragments; and
   (g) preparing subject PRF in the exact manner the reference PRF was prepared in steps (a) and (b) and repeating steps (c)–(f) using said labeled subject PRF in place of said labeled reference PRF;
   (h) comparing output of steps (f) and (g) for performing the steps of recognizing polymorphisms within said partially purified polymorphic subject fragments.

2. The method as defined in claim 1 wherein said distinct labels comprise biochemical and/or isotopic labels.

3. The method as defined in claim 1 wherein said macromolecules comprise two duplex genomic DNAs.

4. The method as defined in claim 1 wherein said macromolecules comprise two double stranded RNA.

5. The method as defined in claim 1 wherein said macromolecules are selected from the group consisting essentially of genomic DNA and double stranded RNA.

6. In a population of double stranded nucleic acid (DNA) derived from a genome which is so complex that its members cannot be resolved by a fractionation process, a method for comparing subject and reference DNAs and effectuating partial purification of unique polymorphic subject restriction fragments from subject and reference populations of representative fragments comprising the steps of:
   (a) cleaving DNAs at specific nucleotide sequences to provide respective subject and reference PRFs;
   (b) distinctively labelling said reference PRF;
   (c) forming a mixture of said labeled reference PRF and said subject PRF;
   (d) fractionating members of said PRFs in said mixture;
   (e) performing a DNA hybridization of said fractionated mixture;
   (f) utilizing said distinct biochemical and/or isotopic labels for separating said reference duplexes and DNA hybrids of said subject and reference PRFs from said polymorphic members of said PRF and achieving said partial purification of said polymorphic members of said subject PRFs and annealing any remaining single subject strands in said partial purification into duplexes;
   (g) preparing subject PRF in the exact manner the reference PRF was prepared in steps (a) and (b) and repeating steps (c)–(f) using said labeled subject PRF in place of said labeled reference PRF; and
   (h) comparing output of steps (f) and (g) for performing the steps of recognizing polymorphisms within said partially purified polymorphic subject fragments.

7. The method as defined in claim 6 wherein said step of converting said subject and reference genomic DNA into respective said PRF comprises cleaving said genomic DNA with any conventional restriction nuclease.

8. The method as defined in claim 6 wherein said step of converting said subject and reference genomic DNA into respective said PRF comprises cleaving said genomic DNA to provide defined fragments, as opposed to randomly broken strands.

9. The method as defined in claim 6 wherein said subject genomic DNA is converted into said subject PRF and said reference genomic DNA is converted into said reference PRF using an isoschizomeric pair of nucleases.

10. The method as defined in claim 6 wherein said subject genomic DNA is converted into said subject PRF using Asp718 and said reference genomic DNA is converted into said reference PRF using KpnI.

11. The method as defined in claim 6 wherein said subject genomic DNA is converted into said subject PRF using KpnI and said reference genomic DNA is converted into said reference PRF using Asp718.

12. The method as defined in claim 6 wherein said distinct biochemical and/or isotopic labels enable selective removal of said reference PRF from said mixture of subject and reference PRF without conferring differential mobilities to genetically identical members of said subject and reference PRFs during said step of fractionation of said PRF members.

13. The method as defined in claim 6 wherein said step of providing distinct labels comprises the step of using photodynamic biotinylation.

14. The method as defined in claim 6 wherein said step of forming said mixture of said labeled reference PRF and said subject PRF comprises using quantities of said mixture compatible with said fractionation step and step of any amplification of said unique polymorphic members of said subject PRF.

15. The method as defined in claim 6 wherein said mixture of said labeled reference PRF and said subject PRF has at least a 1:1 ratio of said labeled reference PRF to said subject PRF.

16. The method as defined in claim 6 wherein said step of fractionating comprises using a fractionation procedure enabling separation of a particular member of said PRFs from the majority of the other constituents of said PRFs.

17. The method as defined in claim 6 wherein said step of fractionating said PRF members enables co-migration of genetically identical members of said subject and reference PRFs.

18. The method as defined in claim 6 wherein said step of performing said DNA hybridization is performed within each fraction formed during said fractionation step.

19. The method as defined in claim 6 wherein said step of performing DNA hybridization comprises denaturing and then annealing said members of said subject and reference PRFs to provide DNA hybrid duplexes of subject and reference DNA strands, pure subject DNA duplexes, pure reference DNA duplexes, and residual single subject and reference DNA strands.

20. In a population of double stranded nucleic acid (DNA) derived from a genome which is so complex that its members cannot be resolved by a fractionation process, a method for comparing subject and reference DNAs and effectuating partial purification of unique polymorphic subject restriction fragments from subject and reference populations of representative fragments (PRFs) comprising the steps of:

(a) cleaving DNAs at specific nucleotide sequences to provide respective subject and reference PFRs;
(b) distinctively labelling said reference PRF;
(c) forming a mixture of said labeled reference PRF and said subject PRF;
(d) fractionating members of said PRFs in said mixture;
(e) performing a DNA hybridization of said fractionated mixture;
(f) utilizing said distinct biochemical and/or isotopic labels for separating said reference PRFs and DNA hybrids of said subject and reference PRFs from said polymorphic members of said subject PRF and achieving said partial purification of said polymorphic members of said subject PRF and annealing any remaining single subject strands in said partial purification into duplexes;
(g) preparing subject PRF in the exact manner the reference PRF were prepared in steps (a) and (b) and repeating steps (c)–(f) using said labeled subject PRF in place of said labeled reference PRF;
(h) comparing output of steps (f) and (g) for performing the steps of recognizing polymorphisms within said partially purified polymorphic subject fragments;
(i) further purifying said polymorphic members of said subject PRF for analytical usage using one or two dimensional fractionations for display purposes, formation of Recombinant DNA and genetic amplification using recombinant DNA cloning, and/or repeating steps (a)–(h).

* * * * *